United States Patent [19]

Grollier et al.

[11] Patent Number: 4,888,027
[45] Date of Patent: * Dec. 19, 1989

[54] PROCESS FOR DYEING KERATINOUS FIBERS WITH 5,6-DIHYDROXYINDOLE IN COMBINATION WITH AN IODIDE AND A HYDROGEN PEROXIDE COMPOSITION AT ALKALINE PH

[75] Inventors: Jean F. Grollier, Paris; Didier Garoche, Levallois-Perret, both of France

[73] Assignee: L'Oreal, Paris, France

[*] Notice: The portion of the term of this patent subsequent to Feb. 14, 2006 has been disclaimed.

[21] Appl. No.: 177,323

[22] Filed: Apr. 4, 1988

[30] Foreign Application Priority Data

Apr. 2, 1987 [LU] Luxembourg ............................ 86833

[51] Int. Cl.$^4$ .............................................. A61K 7/13
[52] U.S. Cl. ............................................ 8/423; 8/406; 8/634
[58] Field of Search ................... 8/404, 405, 406, 423, 8/634

[56] References Cited

U.S. PATENT DOCUMENTS 1,677,508  7/1928  Winogradoff .
4,208,183  6/1980  Grollier et al. ........................ 8/609
4,746,322  5/1988  Herlihy ................................. 8/406

FOREIGN PATENT DOCUMENTS 2028818  12/1970  Fed. Rep. of Germany .
1166172   6/1958   France .
1264707   5/1961   France .
 823503  11/1959   United Kingdom .
2132642   7/1984   United Kingdom .
2185498   7/1987   United Kingdom .

Primary Examiner—Paul Lieberman
Assistant Examiner—Linda D Skaling
Attorney, Agent, or Firm—Cushman, Darby & Cushman

[57] ABSTRACT

Process for dyeing keratinous fibres, characterized in that there is applied to these fibres at least one composition (A) containing, in an appropriate medium for dyeing, 5,6-dihydroxyindole in combination with iodide ions, the application of this composition (A) being preceded or followed by the application of a composition (B) which contains, in an appropriate medium for dyeing, hydrogen peroxide at an alkaline pH of less than 12.

19 Claims, No Drawings

PROCESS FOR DYEING KERATINOUS FIBERS WITH 5,6-DIHYDROXYINDOLE IN COMBINATION WITH AN IODIDE AND A HYDROGEN PEROXIDE COMPOSITION AT ALKALINE PH

The present invention relates to a new process for coloring keratinous, and in particular human, fibers with 5,6-dihydroxyindole and to the compositions employed in this process.

It is well known that the natural biosynthesis of eumelanins from tyrosine takes place in a number of stages. One of these consists of the formation of 5,6-dihydroxyindole which oxidizes to give a pigment which is one of the main constituents of eumelanin.

Hair-dyeing processes employing 5,6-dihydroxyindole or some of its derivatives have already been proposed in the past.

Thus, in French Pat. No. 1,166,172, a solution of 5,6-dihydroxyindole is applied to hair at an acidic pH for 5 to 60 minutes and, without rinsing, and after rough drying, the color is developed by means of an oxidizing agent which may be, in particular, hydrogen peroxide.

According to French Pat. No. 1,133,594, an alkaline solution of 5,6-dihydroxyindole, optionally containing an oxidizing agent or an oxidation catalyst is applied to hair. Various oxidizing agents including hydrogen peroxide and oxidation catalysts such as cupric chloride are envisaged.

In accordance with this process, it is also possible to operate in two steps by following the application of 5,6-dihydroxyindole in alkaline medium by a rinse and a development by an oxidation catalyst.

French Patent Application No. 2,536,993 has also proposed a dyeing process with a number of steps separated by rinses and consisting in applying, in one stage, a solution of a metal salt at alkaline pH and, in another stage, a solution of 5,6-dihydroxyindole.

After rinsing or shampooing, these two stages are followed or otherwise by the application of hydrogen peroxide in order to determine the final tint by lightening.

These processes of the estate of the art have various disadvantages insofar as they result either in shades which are not very strong despite long application times, or in the production of strong tints but requiring a long application time and resulting in a surface-dyeing which is not very resistant. The use of certain metal salts of groups III to VIII of the Periodic Classification, whose harmlessness is not always demonstrated, can result, under the conditions of use, in the modification of the cosmetic or mechanical properties of the hair.

5,6-Dihydroxyindole-based compositions exhibit, furthermore, problems of stability in storage, especially in alkaline medium.

The applicants have now found, and this forms the subject of the invention, means making it possible to obtain strong tints with 5,6-dihydroxyindole with short application times, without using metal or metal salt of groups III to VIII of the Periodic Table.

Another subject of the invention consists of "kits" or dyeing outfits with a number of components employing these various compounds.

Other subjects of the invention will become apparent from reading the description and the examples which follow.

The process for dyeing keratinous, preferably human, fibers, in accordance with the invention, is essentially characterized in that there is applied to these fibers at least one composition (A) containing, in an appropriate medium for dyeing, 5,6-dihydroxyindole in combination with iodide ions, the application of this composition (A) being preceded or followed by the application of a composition (B) which contains, in an appropriate medium for dyeing, hydrogen peroxide at an alkaline pH of less than 12, preferably less than 11.

According to an embodiment of the invention, the composition containing hydrogen peroxide may also contain at least one oxidation dye.

The applicants have found, in particular, that, by virtue of this process, it is possible to obtain strong and black colors in times which are very short when compared with the process described, inter alia, in French Pat. No. 1,166,172.

Furthermore, the use of longer application times of composition (B) which, according to the state of the art, resulted in the production of dark tints, makes it possible, on the contrary, in the process according to the invention, to obtain a lightening and possibilities of tinting, especially when the alkaline composition (B) containing hydrogen peroxide also contains oxidation dyes.

Within the scope of the process according to the invention, the application of compositions (A) and (B) may be separated or otherwise by a stage of rinsing with water.

The iodide ion is preferably an alkali or alkaline earth metal or ammonium iodide, and more particularly a potassium iodide.

The preferred embodiment of the invention consists in applying, in the first stage, the composition (A) containing the iodide ions in the form of alkali or alkaline-earth metal or ammonium iodide and 5,6-dihydroxyindole, and then the composition (B) containing hydrogen peroxide in alkaline medium in combination or otherwise with an oxidation dye.

The process is preferably applied to the dyeing of hair and in particular of living human hair, in which case the medium employed must be cosmetically acceptable.

The particularly preferred embodiment comprises a stage of rinsing the fibres between the two stages, and this makes it possible, inter alia, to avoid staining the scalp when the composition is employed for dyeing human hair.

In the compositions employed in the process according to the invention, 5,6-dihydroxyindole is generally present in proportions of between 0.01 and 5% by weight, and preferably between 0.03 and 3% by weight based on the weight of the composition (A). The proportion of iodide in the composition (A) applied during the process according to the invention is between 0.007 and 4% by weight, expressed as $I^-$ ions and preferably between 0.08 and 2.5% based on the total weight of the composition (A).

The 5,6-dihydroxyindole/$I^-$ ratio is preferably between 0.05 and 10 and more particularly between 0.5 and 2.

Hydrogen peroxide is present in the composition (B) in proportions which are generally between 1 and 40 volumes and preferably between 2 and 20 volumes and more particularly between 3 and 15 volumes.

As indicated above, this composition may contain oxidation dyes.

The oxidation dyes are not dyes in themselves; they are intermediate compounds which are initially weakly colored or colorless and which are commonly referred to as "oxidation base or precursors", which develop their tinctorial power in an oxidizing medium generally consisting of hydrogen peroxide to give rise, in basic medium, to a dye, according to a process of oxidative condensation, either of the oxidation dye precursor with itself, or of this same precursor with a compound known as "tinter" or "coupler".

Such dyes are well-known in the state of the art and it is possible to mention more particularly oxidation dyes of the para or ortho type, consisting of para-phenylenediamines, para-aminophenols, para-diphenols, orthoaminophenols, ortho-phenylenediamines, ortho-diphenols or heterocyclic derivatives. The tinters or couplers are generally chosen from phenols, such as meta-diphenols, meta-aminophenols, meta-phenylenediamines, mono- or polyhydroxylated derivatives of naphthalene and pyrazolones. It is also possible to mention oxidation dyes capable of being rapidly oxidized such as trihydroxylated benzene derivatives or mono- or diamino di- or monohydroxybenzenes.

The process according to the invention is employed by providing application times in the case of the composition (A) containing 5,6-dihydroxyindole in combination with the iodide ions, of between 10 seconds and 45 minutes and preferably of the order of 2 to 25 minutes and more particularly in the region of 2 to 15 minutes, and in the case of the composition (B) containing hydrogen peroxide, application times of between 10 seconds and 45 minutes and preferably between 1 minute and 30 minutes.

The applicant have found that the process employed made it possible to obtain colors which are both rapid and strong, with good penetration of the fibers, especially of human keratinous fibers such as hair, in relatively short times of the order of 5 to 15 minutes.

The process according to the invention also makes it possible to obtain light tints, either by employing low concentrations of 5,6-dihydroxyindole and iodide within the limit of the indicated 5,6-dihydroxyindole/I⁻ ratio and very short application times for the application of the hydrogen peroxide composition (B), or by lightening dark tints which have already been obtained by applying the hydrogen peroxide composition (B) at alkaline pH in a prolonged manner.

The applicant have found, furthermore, that hair dyed a number of times following its regrowth, with the process and the compositions according to the invention, was softer, and more glossy than the hair dyed using the processes and the compositions of the prior art.

The compositions employed for making use of the process according to the invention may take various forms, such as liquids which are more or less thickened or gelled, creams, emulsions, foams or other appropriate forms for effecting dyeing.

The dye compositions intended to be employed in the process according to the invention and containing either 5,6-dihydroxyindole in combination with iodide ions or hydrogen peroxide, generally contain an aqueous medium consisting of water or of a water-solvent(s) mixture, the solvent(s) being preferably chosen from organic solvents such as ethyl alcohol, propyl or isopropyl alcohol, tert-butyl alcohol, ethylene glycol, ethylene glycol monomethyl, monoethyl or monobutyl ethers, ethylene glycol monoethyl ether acetate, propylene glycol, the monomethyl ethers of propylene glycol and of dipropylene glycol and methyl lactate.

The preferred solvents are ethyl alcohol and propylene glycol.

The composition (A) has a pH of between 2 and 7 and preferably between 3.5 and 7.

As indicated above, the composition (B) has an alkaline pH of less than 12 and preferably between 8 and 11.

It is also possible to store 5,6-dihydroxyindole and/or the iodide in a medium consisting of essentially anhydrous solvents and to mix this medium or these media with an aqueous medium at the time of use. The solvents are chosen from those mentioned above.

The term anhydrous solvent is applied to a solvent containing less than 1% of water.

When the medium consists of a water-solvent(s) mixture, the solvents are present in concentrations of between 0.5 and 75%, in particular between 2 and 50% by weight, based on the total weight of the composition, and more particularly between 2 and 20%.

The compositions employed in accordance with the invention may contain fatty amides such as mono- or diethanolamides of acids derived from copra, of lauric acid, or of oleic acid, in concentrations of between 0.05 and 10% by weight.

They may also contain anionic, cationic, nonionic or amphoteric surface-active agents, or mixtures thereof.

These surface-active agents are preferably employed in proportions of between 0.1 and 50% by weight based on the total weight of the composition, and advantageously between 1 and 20% by weight.

The compositions defined above and employed in the process in accordance with the invention may be thickened with thickening agents such as sodium alginate, gum arabic, guar gum, biopolymers such as xanthan gum or scleroglucans, cellulose derivatives such as methyl cellulose, hydroxyethyl cellulose or hydroxypropyl methyl cellulose, the sodium salt of carboxymethyl cellulose and acrylic acid polymers. It is also possible to employ inorganic thickening agents such as bentonite. These thickeners are employed by themselves or mixed and are preferably present in proportions of between 0.1 and 5% by weight based on the total weight of the composition, and advantageously between 0.5 and 3%.

The alkalizing agents which may be employed in these compositions may be, in particular, amines such as alkanolamines, alkylamines, and alkali metal or ammonium hydroxides or carbonates. The acidifying agents which may be employed may be chosen from lactic acid, acetic acid, tartaric acid, phosphoric acid, hydrochloric acid and citric acid, but it is possible, of course, to employ other alkalizing or acidifying agents which are suitable for dyeing.

An advantageous embodiment of the invention consists in employing an alkanolamine such as monoethanolamine as an alkalizing agent for the composition (B).

It is possible, if desired, to add an agent for swelling the keratinous fiber, such as, for example, urea, to each of the compositions.

When the composition containing 5,6-dihydroxyindole is employed in the form of foam, it may be packaged under pressure in an aerosol device in the presence of a propellent agent and of a foam generator. The foam generating agents may be anionic, cationic, nonionic or amphoteric foaming polymers or surface-active agents as indicated above.

The compositions employed in the process in accordance with the invention may additionally contain various adjuvants such as perfumes, sequestering agents, film-forming agents, fiber-treatment agents, dispersing agents, conditioning agents, preserving agents, and opacifiers.

With a view to making use of the process according to the invention, the compositions may be packaged in multicompartment devices also known as "kits" or dyeing outfits comprising all the components intended to be applied for a single dyeing treatment of the keratinous fibers in successive applications with or without premixing.

Such devices are known per se and may comprise a first compartment containing the 5,6-dihydroxyindole composition in the presence of iodide ions in an appropriate medium for the dyeing, a hydrogen peroxide solution in a second compartment, and, in a third compartment, an alkalizing agent intended to be mixed at the time of use with the contents of the second compartment in order to produce a hydrogen peroxide composition at an alkaline pH.

According to a particular embodiment, this multicompartment device may contain an oxidation dye in an appropriate medium for the dyeing, in the third compartment comprising the alkalizing agent. It is also possible to provide a fourth compartment containing the oxidation dye in an appropriate medium for the dyeing, the contents either of the third and of the second compartments or of the fourth, third and second compartments being mixed just before use.

If the medium containing 5,6-dihydroxyindole consists of an anhydrous solvent, then, before use, mixing is carried out with an aqueous medium which is appropriate for the dyeing and present, if desired, in a fifth compartment.

5,6-Dihydroxyindole in anhydrous medium may also be applied directly to moist keratinous fibers.

According to another embodiment, the dyeing "kit" or outfit comprises a first compartment enclosing a composition containing iodide ions in an appropriate medium or dyeing, a second compartment enclosing a composition containing 5,6-dihydroxyindole in an appropriate medium for dyeing, a third compartment enclosing a hydrogen peroxide solution, a fourth compartment enclosing an alkalizing agent and, if desired, oxidation dyes and, if desired, a fifth compartment enclosing oxidation dyes. The composition contained in the second compartment is intended to be mixed, at the time of use, with the content of the first compartment, and that contained in the fourth and, if desired, the fifth compartment is intended to be mixed extemporaneously with that in the third.

These devices may be equipped with mixing means which are known per se, and may be packaged under an inert atmosphere.

The processes according to the invention and the corresponding compositions may be employed for dyeing natural hair or hair which has already been dyed, permanent-waved or otherwise or straightened or hair which is strongly or lightly bleached and, if desired, permanent-waved. In this case, the coloring treatments may be preceded or followed by other cosmetic treatments known per se.

It is also possible to use them to dye furs or wool.

The following examples are intended to illustrate the invention without, however, being of a limiting nature.

EXAMPLE 1

Coloring of natural 90% white hair is carried out by successively applying two compositions (A) and (B), separated by an intermediate rinse.

The hair is impregnated for 15 minutes with the following composition (A):

5,6-dihydroxyindole: 2.00 g
potassium iodide: 2.00 g
ethyl alcohol: 10.00 g
water q.s.: 100 g
spontaneous pH=6.5:

After rinsing with water, a 10-volume hydrogen peroxide composition (B) adjusted to pH 10 with $NH_4OH$ is applied. The composition (B) is left in place for 5 minutes and rinsing with water and drying are then performed. A black color is obtained.

EXAMPLE 2

Example 1 is reproduced with the difference that the 10-volume, pH 10, hydrogen peroxide composition (B) is left in place for 10 minutes instead of 5. A dark coloration is obtained.

EXAMPLE 3

Example 1 is reproduced, with the difference that the 10-volume, pH 10, hydrogen peroxide composition (B) is left in place for 15 minutes instead of 5. A dark chestnut brown coloration is obtained.

EXAMPLE 4

Example 1 is reproduced with the difference that the 10-volume, pH 10, hydrogen peroxide composition (B) is left in place for 30 minutes instead of 5. A chestnut brown coloration is obtained.

EXAMPLE 5

Permanent-waved 90% white hair is colored by successively applying two compositions (B) and (A).

The hair is impregnated for 10 minutes with the 10-volume hydrogen peroxide composition (B) adjusted to pH 10 with $NH_4OH$.

The hair is not rinsed with water and the composition (A) described in Example 1 is then applied and is left in place for 15 minutes.

After rinsing with water and drying, the hair is dyed dark grey.

EXAMPLE 6

Permanent-waved 90% white hair is colored by successively applying two compositions (A) and (B), which are separated by an intermediate rinse.

The hair is impregnated for 15 minutes with the following composition (A):

5,6-dihydroxyindole: 2.5 g
potassium iodide: 2.00 g
ethyl alcohol: 10.00 g
guar gum sold by Celanese under the name Jaguar HP 60: 1.00 g
glycoside alkyl ether sold at the concentration of 60% of AS by Seppic under the name "Triton CG 110": 5.00 g AS
water q.s.: 100 g
spontaneous pH=6.5:

The hair is rinsed with water

A composition (B) corresponding to the following composition is then applied and left in place for 30 minutes:

Composition (B):

This composition (B) is produced extemporaneously mixing 2/1 of 20-volume $H_2O_2$ (66 g) and 33 g of the composition:

nonylphenol oxyethylenated with 4 moles of ethylene oxide: 24.0 g
nonylphenol oxyethylenated with 9 moles of ethylene oxide: 20.0 g
oleic diethanolamine: 4.0 g
2-butoxyethanol: 12.0 g
propylene glycol: 7.0 g
complexing agent: 0.1 g
aqueous ammonia solution containing 20% $NH_3$: 17.0 g
water q.s.: 100 g
spontaneous pH=11.3

The pH of the composition (B) after mixing is 10.

After rinsing with water and drying, the hair is dyed brown with mahogany-colored highlights.

EXAMPLE 7

Example 4 is reproduced with the difference that a 20-volume, instead of 10-volume, hydrogen peroxide solution is employed. A light chestnut brown coloration is obtained.

EXAMPLE 8

Example 4 is reproduced with the difference that a volume, instead of 10-volume, hydrogen peroxide solution is employed. A golden beige light blond coloration is obtained.

EXAMPLE 9

Permanent-waved 90% white hair is colored by successively applying two compositions (A) and (B) which are separated by an intermediate rinse.

The hair is impregnated for 15 minutes with the following composition (A):

5,6-dihydroxyindole: 2.5 g
potassium iodide: 2.0 g
ethyl alcohol: 10.0 g
guar gum sold by Celanese under the name "Jaguar HP 60": 1.0 g
glycoside alkyl ether sold at the concentration of 60% of AS by Seppic under the name "Triton CG 110" 5.0 g AS
water q.s.: 100 g
spontaneous pH=6.5:

The hair is rinsed with water.

A composition (B) corresponding to the following composition is then applied and left in place for 15 minutes:

Composition (B):

This composition (B) is produced extemporaneously by mixing 1/1 of 12.5-volume $H_2O_2$ (50 g) and 50 g of the composition: Nonionic surfactant of formula:

$$C_{18}H_{36}O + C_2H_3O - (CH_2OH) \frac{1}{n} H$$

prepared according to French Patent No. 1,477,048 4.5 g
2-butoxyethanol: 5.0 g
ammonium lauryl sulphate: 7.0 g
copra diethanolamide sold by Henkel under the name "Comperlan KD": 10.0 g
propylene glycol: 7.0 g
N,N-dimethyl-1-dodecaneamine N-oxide sold at a concentration of 30% AS by Onyx under the name "Ammonyx LO": 2.0 g AS
sequestering agent: 1.5 g
aqueous ammonia solution containing 20% $NH_3$: 7.4 g
water q.s.: 100 g
spontaneous pH=10.6:

The pH of the composition (B) after mixing is about 10.2.

After rinsing with water and drying, the hair is dyed black.

EXAMPLE 10

Natural 90% white hair is colored by successively applying two compositions (A) and (B) which are separated by an intermediate rinse.

The hair is impregnated for 15 minutes with the following composition (A):

5,6-dihydroxyindole: 2.5 g
potassium iodide: 2.0 g
ethyl alcohol: 10.0 g
guar gum sold by Celanese under the name "Jaguar HP 60": 1.0 g
glycoside alkyl ether sold at the concentration of 60% of AS by Seppic under the name "Triton CG 110": 5.0 g AS
water q.s.: 100 g
spontaneous pH=6.5:

The hair is rinsed with water.

A composition (B) corresponding the following composition is then applied and left in place for 30 minutes:

Composition (B):

This composition (B) is produced extemporaneously by mixing 1/1 of 20-volume $H_2O_2$ (50 g) and 50 g of the composition:

triethanolamine lauryl sulphate containing 40% of AS: 4.5 g AS
oleyl alcohol: 8.0 g
oleic diethanolamide: 10.0 g
oleocetyl alcohol with 30 moles of EO marketed by Henkel under the name of "Mergital OC 30": 4.0 g
oleic acid: 17.0 g
Cationic polymer described and prepared according to French Pat. No. 2,270,846, consisting of repeat units of formula:

$$\left[ \begin{array}{c} CH_3 \\ | \\ -\oplus N-(CH_2)_3-\oplus N-(CH_2)_6- \\ | \\ CH_3 \quad Cl^{\ominus} \end{array} \begin{array}{c} CH_3 \\ | \\ \\ | \\ CH_3 \quad Cl^{\ominus} \end{array} \right] \quad 3.5 \text{ g AS}$$

Benzyl alcohol: 8.0 g
96° ethyl alcohol: 10.0 g
22° Be aqueous ammonia: 9.0 ml
Monoethanolamine: 7.0 g
p-Aminophenol base: 0.70 g
m-Diaminoanisole sulphate: 0.15 g
Resorcinol: 0.15 g
m-Aminophenol base: 0.15 g
Nitro-p-phenylenediamine: 0.015 g
p-Toluylenediamine: 0.30 g
Ethylenediaminetetraacetic acid sold under the name "Trilon B": 3.0 g
Sodium bisulphite (d=1.32): 1.2 g
Water q.s.: 100 g The pH of composition (B) after mixing is 9. After rinsing with water and drying, the hair is dyed dark chestnut brown.

EXAMPLE 11

Natural 90% white hair is coloured by successively applying two compositions (A) and (B) which are separated by an intermediate rinse.

The hair is impregnated for 15 minutes with the following composition (A):
5,6-dihydroxyindole: 3 g
sodium iodide: 3 g
ethylene glycol monobutyl ether: 10 g
xanthan gum sold by Rhone-Poulenc under the name Rhodopol SC: 2 g
glycoside alkyl ether sold at the concentration of 60% AS by Seppic under the name "Triton C.G 110": 2.1 g AS
water q.s.: 100 g
spontaneous pH=4.6:
The hair is rinsed with water.

A composition (B) of 20-volume hydrogen peroxide at pH 10 adjusted with monoethanolamine is then applied and left in place for 15 minutes.

After rinsing with water and drying, the hair is dyed golden blond.

We claim:

1. A plural stage process for dyeing keratinous fibers comprising applying to said fibers, in an amount effective to dye said keratinous fibers, a composition (A) containing, in an appropriate medium for dyeing, 5,6-dihydroxyindole, present in an amount ranging from 0.01 to 5 percent by weight, based on the total weight of said composition (A), and iodide ions, present in an amount ranging from 0.007 to 4 percent by weight, expressed as I- ions, based on the total weight of said composition (A), the application of said composition (A) being preceded or followed by applying to said fibers composition (B) containing, in an appropriate medium for dyeing, hydrogen peroxide at a concentration ranging from 1 to 40 volumes, at an alkaline pH of less than 12.

2. The process of claim 1 wherein said composition (B) also contains at least one oxidation dye selected from the group consisting of a paraphenylenediamine, a para-aminophenol, a paradiphenol, an ortho-aminophenol, an ortho-phenylenediamine, an ortho-diphenol and a heterocyclic derivative.

3. The process of claim 2 wherein said composition (B) also contains a tinter or coupler selected from the group consisting of a meta-diphenol, a meta-aminophenol, a metaphenylenediamine, a monohydroxynaphthalene derivative, a polyhdyroxynaphthalene derivative and a pyrazolone.

4. The process of claim 1 wherein said composition (B) also contains an oxidation dye capable of being rapidly oxidized and selected from the group consisting of a trihydroxylated benzene derivative, a monoamino dihydroxybenzene, a monoamino monohydroxy benzene, a diamino dihydroxybenzene and a diamino monohydroxybenzene.

5. The process of claim 1 wherein said iodide ions are selected from the group consisting of alkali metal iodides, alkaline earth metal iodides and ammonium iodides.

6. The process of claim 1 wherein the weight ratio of said 5,6-dihydroxyindole to said iodide ions ranges from 0.05 to 10.

7. The process of claim 1 wherein the application of compositions (A) and (B) is separated by a rinsing stage.

8. The process of claim 1 comprising, in a first stage, applying composition (A) containing iodide ions in the form of an alkali metal iodide, an alkaline earth metal iodide or an ammonium iodide, and said 5,6-dihydroxyindole and, in a subsequent stage, applying said composition (B) containing hydrogen peroxide at an alkaline pH less than 12.

9. The process of claim 1 wherein said composition (A), containing said 5,6-dihydroxyindole and said iodide ions, is applied to said fibers with an exposure time ranging from 10 seconds to 45 minutes, and wherein said composition (B), containing said hydrogen peroxide, is applied to said fibers with an exposure time ranging from 10 seconds to 45 minutes, the time selected being dependent on the shade desired.

10. The process of claim 1 wherein said compositions (A) and (B) are in the form of a thickened or gelled liquid, a cream, an emulsion or a foam.

11. The process of claim 1 wherein said appropriate medium of compositions (A) is water or a mixture of water and an organic solvent, said composition (A) having a pH ranging from 2 to 7.

12. The process of claim 1 wherein said composition (A) is in the form of a solution in an anhydrous solvent medium.

13. The process of claim 11 or 12 wherein said solvent is selected from the group consisting of ethyl alcohol, propyl alcohol, isopropyl alcohol, tert. butyl alcohol, ethylene glycol, ethylene glycol monomethyl ether, ethylene glycol monoethyl ether, ethylene glycol monobutyl ether, ethylene glycol monoethyl ether acetate, propylene glycol, monomethyl ether or propylene glycol, monomethyl ether of dipropylene glycol and methyl lactate.

14. The process of claim 1 wherein one or both of said compositions (A) and (B) contain at least one adjuvant selected from the group consisting of
(a) a fatty amide present in an amount ranging from 0.05 to 10 weight percent,
(b) an anionic, cationic, nonionic or amphoteric surfaceactive agent, or a mixture thereof, present in an amount ranging from 0.1 to 50 weight percent,
(c) a thickening agent present in an amount ranging from 0.1 to 5 weight percent,
(d) a perfume,
(e) a sequestering agent,
(f) a film-forming agent,
(g) a dispersing agent,
(h) a preservative,
(i) an opacifier and
(j) an agent for swelling said keratinous fibers.

15. The process of claim 1 wherein said keratinous fibers are human hair.

16. A keratinous fiber multicompartment dyeing kit comprising
one first compartment containing a composition comprising, in an appropriate medium for dyeing, 5,6-dihydroxyindole, present in an amount ranging from 0.01 to 5 percent by weight based on the total weight of said composition, and iodide ions, present in an amount ranging from 0.007 to 4 percent by weight, expressed as I- ions, based on the total weight of said composition,
a second compartment containing a composition comprising, in an appropriate medium for dyeing, hydrogen peroxide at a concentration ranging from 1 to 40 volumes, and a third compartment containing an aqueous medium at an alkaline pH, the contents of said third compartment intended to be mixed with the contents of said second compartment just before dyeing said keratinous fibres.

17. The keratinous fiber dyeing kit of claim 16 wherein said third compartment also contains an oxidation dye selected from the group consisting of a paraphenylene diamine, a para-aminophenol, a para-diphenol, an ortho-aminophenol, an ortho-phenylenediamine, an ortho-diphenol and a heterocyclic derivative.

18. The keratinous fiber dyeing kit of claim 16 which also includes a fourth compartment containing an oxidation dye in an appropriate medium for dyeing, the contents of said fourth compartment intended to be mixed with the contents of said third compartment and with the contents of said second compartment just before dyeing said keratinous fibers.

19. A keratinous fiber multicompartment dyeing kit comprising a first compartment containing a composition comprising in an appropriate medium for dyeing, iodide ions, present in an amount ranging form 0.007 to 4 percent by weight, expressed as $I^-$ ions, based on the total weight of said composition, a second compartment containing a composition comprising, in an appropriate medium for dyeing, 5,6-dihydroxyindole present in an amount ranging from 0.01 to 5 percent by weight based on the total weight of said composition, a third compartment containing a composition comprising, in an appropriate medium for dyeing, hydrogen peroxide at a concentration ranging from 1 to 40 volumes, and a fourth compartment containing an aqueous alkaline medium at a pH less than 12.

the contents of said fourth compartment intended to be mixed with the contents of said third compartment, and the contents of said second compartment intended to be mixed with the contents of said first compartment, just before dyeing said keratinous fibers.

* * * * *